(12) United States Patent
O'Brien et al.

(10) Patent No.: US 9,456,847 B2
(45) Date of Patent: Oct. 4, 2016

(54) CERVICAL CERCLAGE ASSISTANCE DEVICE

(71) Applicant: Cook Medical Technologies LLC, Bloomington, IL (US)

(72) Inventors: John M. O'Brien, Lexington, KY (US); Matthew J. Terwiske, Bloomington, IN (US); Justin D. Renfrow, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 395 days.

(21) Appl. No.: 13/795,510

(22) Filed: Mar. 12, 2013

(65) Prior Publication Data

US 2013/0239974 A1     Sep. 19, 2013

Related U.S. Application Data

(60) Provisional application No. 61/610,263, filed on Mar. 13, 2012.

(51) Int. Cl.
*A61B 17/42* (2006.01)
*A61B 17/12* (2006.01)
*A61B 17/00* (2006.01)

(52) U.S. Cl.
CPC .......... *A61B 17/42* (2013.01); *A61B 17/12136* (2013.01); *A61B 17/4241* (2013.01);
(Continued)

(58) Field of Classification Search
CPC ............ A61F 6/08; A61F 6/146; A61F 6/16; A61F 6/18; A61F 5/4407; A61F 5/4408; A61B 17/42; Y10T 403/58; Y10T 403/581; Y10T 403/583; Y10T 403/585; Y10T 403/587; Y10T 403/65; Y10T 403/655; Y10T 403/66; Y10T 403/75; Y10T 403/70162
USPC .......................... 606/119; 128/830, 834, 839
See application file for complete search history.

(56) References Cited

U.S. PATENT DOCUMENTS

| 4,128,100 A | 12/1978 | Wendorff | ................... 128/335.5 |
| 5,591,203 A | 1/1997 | Fahy | ............................. 606/207 |

(Continued)

FOREIGN PATENT DOCUMENTS

| CN | 201 806 769 U | 4/2011 |
| CN | 202 920 311 U | 5/2013 |

(Continued)

OTHER PUBLICATIONS

International Search Report for PCT/US2013/030320, dated Jul. 12, 2013.

(Continued)

*Primary Examiner* — Victoria J Hicks
*Assistant Examiner* — Camtu Nguyen
(74) *Attorney, Agent, or Firm* — Brinks Gilson & Lione

(57) ABSTRACT

A medical device configured for assistance with the cervical cerclage procedure is provided. The medical device includes a barrier structure with a finger and a therebetween. A hub is fixed to a distal end of the catheter and defines an extension with a second void between an end surface of the hub and the extension. The barrier structure and the hub are releaseably attached with the extension disposed within the first void and the finger within the second void. A wire guide withdrawably extends through coaxial holes within the hub, extension, finger, and a portion of the barrier structure to fix the hub and barrier structure together.

15 Claims, 15 Drawing Sheets

(52) U.S. Cl.
CPC ............... *A61B2017/00473* (2013.01); *A61B 2017/00477* (2013.01); *A61B 2017/00557* (2013.01); *A61B 2017/4225* (2013.01)

(56) References Cited

U.S. PATENT DOCUMENTS

| | | | |
|---|---|---|---|
| 5,925,059 A * | 7/1999 | Palermo et al. | 606/191 |
| 6,063,100 A * | 5/2000 | Diaz et al. | 606/191 |
| 6,132,388 A * | 10/2000 | Fleming | A61M 25/09 600/585 |
| 7,105,007 B2 | 9/2006 | Hibler | 606/193 |
| 2004/0092847 A1 | 5/2004 | Welch | |
| 2004/0127931 A1 | 7/2004 | Kincaid et al. | 606/193 |
| 2005/0125006 A1 | 6/2005 | Nady | 606/119 |
| 2005/0277948 A1 | 12/2005 | Cedars et al. | 606/119 |
| 2008/0188863 A1 | 8/2008 | Chu | 606/119 |
| 2009/0142844 A1 | 6/2009 | Le Comte | |
| 2009/0306588 A1 | 12/2009 | Nguyen et al. | |
| 2011/0079226 A1 * | 4/2011 | Sakhel | 128/830 |
| 2013/0103044 A1 | 4/2013 | Brown | |
| 2013/0239974 A1 | 9/2013 | O'Brien et al. | |

FOREIGN PATENT DOCUMENTS

| | | | | |
|---|---|---|---|---|
| DE | 43 02 895 A1 | 8/1994 | | |
| WO | WO 2006/117612 A1 | 11/2006 | ............ | A61M 27/00 |
| WO | WO 2010/114577 A1 | 10/2010 | ............... | A61F 2/00 |

OTHER PUBLICATIONS

Patent Examination Report, IP Australia, for AU 2013232405, dated Jan. 13, 2015, 3 pages.
International Preliminary Report on Patentability and Written Opinion for PCT/US2013/030320, date of issuance: Sep. 16, 2014, 7 pages.
Extended European Search Report for 15 190 350.7, dated Feb. 25, 2016, 7pp.

* cited by examiner

CERVICAL CERCLAGE ASSISTANCE DEVICE

CROSS-REFERENCE TO RELATED APPLICATIONS

This application claims priority from U.S. Provisional Application No. 61/610,263, filed on Mar. 13, 2012, the entirety of which is hereby fully incorporated by reference herein.

TECHNICAL FIELD

The cervical cerclage procedure is often indicated for expecting female patients that have an incompetent cervix, or a cervix that is incapable of remaining closed during pregnancy, prior to the onset of labor. The cerclage procedure most often involves the physician vaginally suturing the patient's cervical tissue closed, or to the neighboring portions of the cervical tissue to prevent fluid or other communication through the cervix and into or out of the uterus prior to the onset of labor. There are several common types of vaginal cerclage stitches, such as the McDonald stitch and the Shirdokar stitch. While these types of cerclage stitches are well known in the art, they are often difficult to perform due to the number of instruments needed to both prepare and compress the cervical tissue to close the cervix prior to the cervical stitching, as well the needles needed to perform the cerclage stitch itself. The patient's vagina includes a relatively small space for all of these tools and therefore the cerclage procedure is overly complicated and time consuming.

BRIEF SUMMARY

A first representative embodiment of the disclosure provides a device for assistance with the cervical cerclage procedure. The device includes a barrier structure configured to allow gripping and compression of a patient's cervical tissue when disposed proximate a patient's cervix. The device additionally includes an elongate catheter with a distal portion with an inflatable balloon and a proximal portion configured to allow selective inflation and deflation of the balloon. The distal portion of the catheter is selectively releasably connected to the barrier structure.

A second representative embodiment of the disclosure provides a device for assistance with the cervical cerclage procedure. The device includes a barrier structure configured to allow gripping and compression of a patient's cervical tissue when disposed proximate a patient's cervix. The barrier structure includes first and second blind holes that each extend within the barrier structure from a base thereof. The first and second holes intersect each other. A catheter is releasably connected to the barrier structure and includes a tip that extends from a distal end thereof and is releasably disposed within the first hole. A wire guide is threaded through a lumen in the catheter and the second hole in the barrier surface to interact with the tip.

A third representative embodiment of the disclosure provides a medical device configured for assistance with the cervical cerclage procedure. The device includes a barrier structure with a finger that extends from a base of the barrier structure to define a first void between the finger and the base, wherein a first hole extends through both the finger and blindly through a portion of the base. The embodiment may include one or more arms that are fixed to the barrier structure to support and align a tape or band around a patient's cervix. A hub is fixed to a distal portion of an elongate catheter, which comprises an extension that extends from an end surface of the hub to define a second void between the end surface of the hub and the extension. A lumen extends through the catheter and further communicates through a blind second hole through the hub and the second finger. The barrier structure and hub are configured to mate together such that the extension extends within the first void and the finger extends within the second void, and such that the lumen, second blind hole, and the first blind hole are coaxially aligned.

A fourth representative embodiment of the disclosure provides a method of performing cervical cerclage. The method includes the steps of inserting a catheter with an inflatable balloon and supporting a removable barrier structure at a distal end portion thereof to a position proximate a patient's cervix, wherein the barrier structure comprises a first aperture with a flexible band disposed therethrough. Aligning the barrier structure such that the flexible band is in registry with the patient's cervix and inflating the balloon to compress the cervical tissue. The method further comprises wrapping the flexible band around the cervical tissue and tying opposite ends of the flexible band to maintain the cervical tissue in a closed configuration and then deflating the balloon, disconnecting the barrier structure from the distal end portion of the catheter, and removing the catheter from the patient. The method further comprises performing one or more vaginal cerclage stitches upon the cervical tissue, and cutting the flexible band and removing the flexible band and barrier structure from the patient.

Advantages of the present disclosure will become more apparent to those skilled in the art from the following description of the preferred embodiments of the disclosure that have been shown and described by way of illustration. As will be realized, the disclosed subject matter is capable of other and different embodiments, and its details are capable of modification in various respects. Accordingly, the drawings and description are to be regarded as illustrative in nature and not as restrictive.

DETAILED DESCRIPTION OF THE DRAWINGS AND THE PRESENTLY PREFERRED EMBODIMENTS

Figure 1:
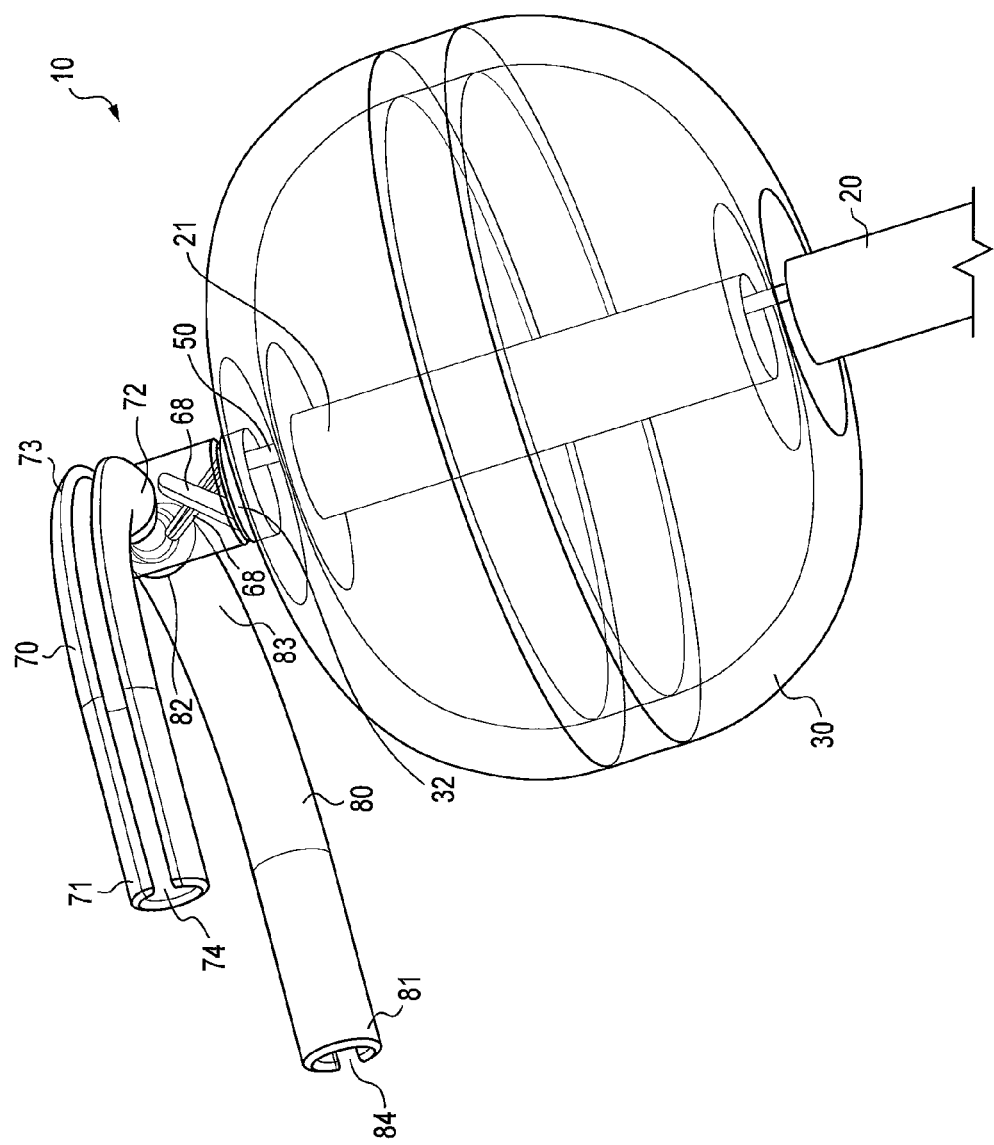
FIG. 1 is a perspective view of a cervical cerclage assistance device, showing a balloon disposed upon a catheter in an inflated configuration.

Turning now to FIGS. 1-7, a cerclage assistance device 10 is provided. The device 10 includes a catheter 20 that extends from a proximal end portion 22 to a distal end portion 21. An inflatable balloon 30, similar to a Foley balloon, is provided at the distal end portion 21. A first lumen 26 is disposed along the length of the catheter 20 to allow for selective inflation of the balloon 30 from the proximal end portion 22 of the catheter 20. The proximal end portion 22 of the catheter may receive a syringe through a luer lock fitting or similar structure (not shown) that is disposed in fluid communication with the first lumen 26 to allow for selective inflation and deflation of the balloon 30. The catheter 20 may additionally include a second lumen 24 along its length between the proximal and distal end portions 22, 21 to allow a wire guide 50 or similar elongate, thin, flexible member therethrough.

Figure 6:
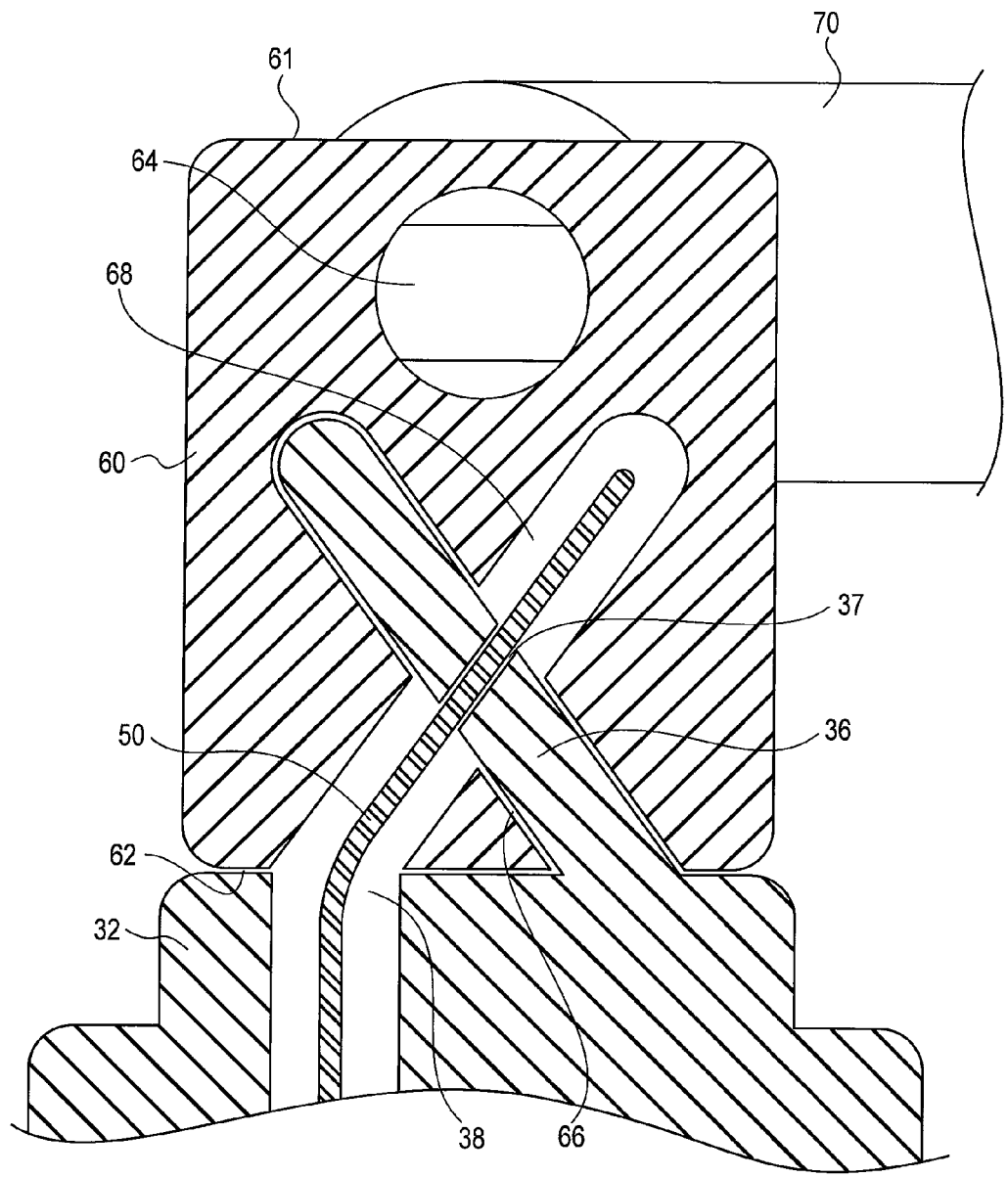
FIG. 6 is a cross-sectional view of the barrier structure and distal end portion of the catheter, with the tip and wire guides engaged within the barrier structure.
Figure 7:
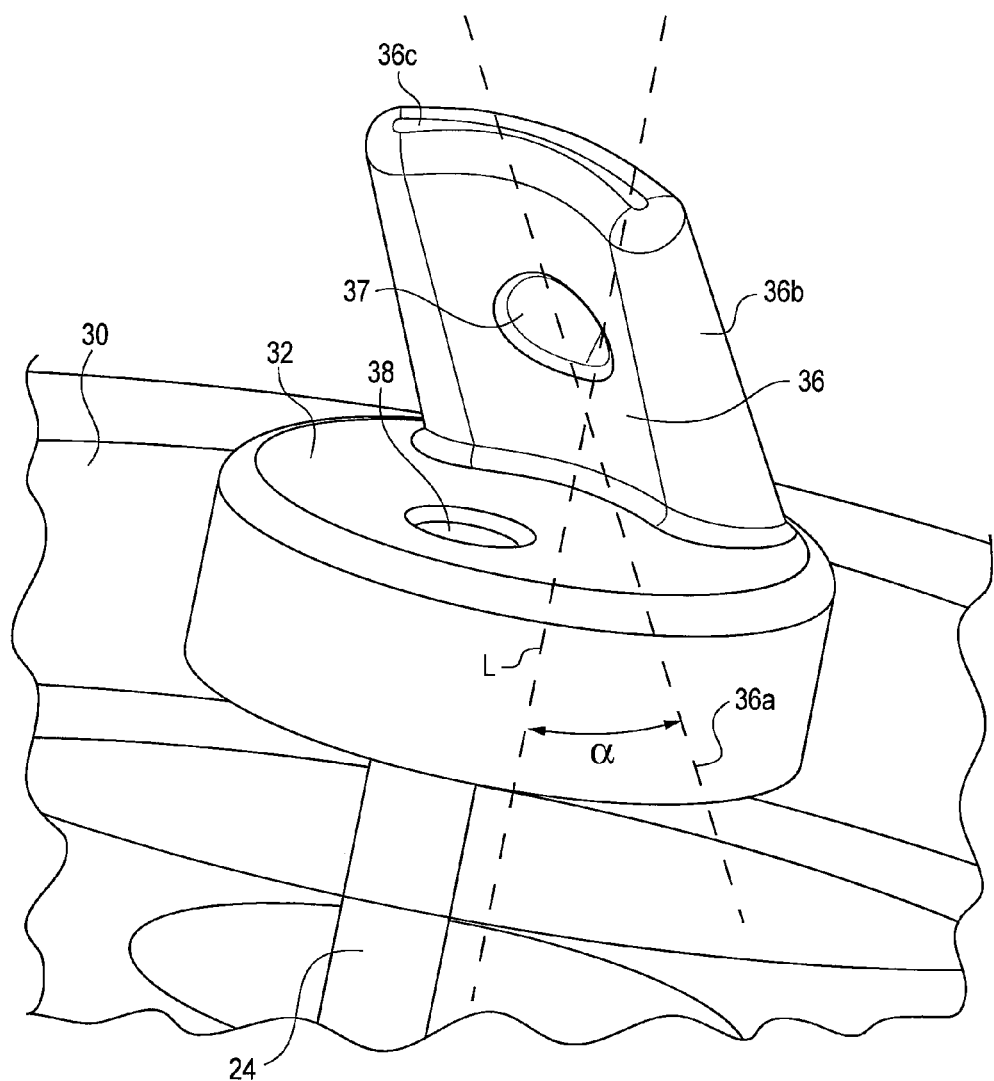
FIG. 7 is a perspective view of the support portion and tip of the catheter of the device of FIG. 1.

The distal end portion 21 of the catheter 20 includes a support portion 32 that may reside upon the catheter 20 distally of the balloon 30, and provide the distal end surface 21a (FIG. 7) of the catheter 20. The support portion 32 includes tip 36 that extends distally from the distal end surface 21a. In some embodiments, the tip 36 extends at an acute angle α with respect to the longitudinal axis L of the catheter 20 at the distal end portion 21 (best shown in FIGS. 6-7), the angle α is measured between the longitudinal axis L and an axis 36a formed through the tip 36. In some embodiments the tip 36 may be substantially straight, that extends along the line 36a, while in other embodiments, the tip 36 may be arcuate and have a changing angle with respect to the longitudinal axis L of the catheter 20 along its length. The tip 36 may have a relatively rectangular cross-section along its length, which may have substantially the same dimensions along its length, or may have decreasing dimensions to reduce the size of the tip 36 as it moves toward the distal end 36c of the tip 36. In some embodiments, the edges 36b of the tip 36 may be chamfered or rounded, as shown in FIG. 7.

The tip 36 may include a first aperture 37 that is disposed through the body of the tip 36. The first aperture 37 is configured to receive a wire guide 50 therethrough, as discussed in greater detail below. The first aperture 37 of the tip 36 is positioned such that the first aperture 37 is in registry with the second hole 68 of the barrier structure 60 when the tip 36 is disposed within the first hole 66 of the barrier structure 60 (discussed in greater detail below) such that a wire guide 50 extending through the second hole 68 additionally extends through the first aperture 37 in the tip 36, as best shown in FIG. 6. The support portion 32 additionally includes a second aperture 38 that is disposed in registry with the second lumen 24 for the wire guide 50 to pass through. The second aperture 38 and the first aperture 37 are each positioned with respect to each other such that a typical wire guide 50, such as a 0.032 inch wire guide extending through the second aperture 38 can easily bend to extend through the first aperture 37.

The catheter 20 is releasably engaged with a barrier structure 60 at the distal end portion 21 of the catheter 20. The barrier structure 60 may include a base 62, or bottom surface, that includes first and second holes 66, 68 that blindly extend within the base 62. The first hole 66 is configured to receive the tip 36 and may be formed with a size and shape just slightly larger than the size and shape of the tip 36, such that the tip 36 easily slides through the first hole 66 when the barrier structure 60 is engaged with the support portion 32 of the catheter 20.

The barrier structure 60 may additionally include a second hole that extends blindly therethrough from the base 62, and may be oriented such that the second hole 68 intersects the first hole 66, as best shown in FIG. 6. The second hole may have a circular or other profile, and have a diameter (or smallest cross-sectional dimension) to allow a 0.032 inch wire guide 50 (or similar diameter wire guide) to pass therethrough. In some embodiments, when the support portion 32 engages the barrier structure 60, and specifically, the tip 36 of the support portion 32 extends through the first hole 66, the second hole 68 of the barrier structure 60 aligns with the second aperture 38 of the support portion 32 and urges the wire guide 50 extending through the second aperture 38 toward and through the first aperture 37 of the tip 36. The engagement of the wire guide 50 into and through the first aperture 37 in the tip 36 locks the barrier structure 60 with respect to the catheter 20. In some embodiments, the device 10 is constructed such that the barrier structure 60 is engaged with the catheter 20 when the medical professional accesses the device 10 from the packaging.

As can be understood with reference to FIGS. 6 and 7, the barrier structure 60 is releasable from the catheter 20, by urging the wire guide 50 proximately, which causes the distal tip of the wire guide 50 to pull out of the first aperture 37 in the tip 36. When the wire guide 50 is pulled out of the first aperture 37, the catheter 20 and the barrier structure 60 can become decoupled. As discussed in greater detail herein, the catheter 20 and the barrier structure 60 are normally decoupled when the barrier structure 60 is either directly (in embodiments with one or more arms 70, 80 extending therefrom) or indirectly (in embodiments without the one or more arms 70, 80) fixed to the patient's cervix, the catheter 20 may be released from the barrier structure 60 by urging the catheter 20 proximally. Because the barrier structure 60 is either directly or indirectly fixed to the patient's cervical tissue, the tip 36 is pulled from the first hole 66 in the barrier structure 60 thereby separating the two components.

Figure 2:
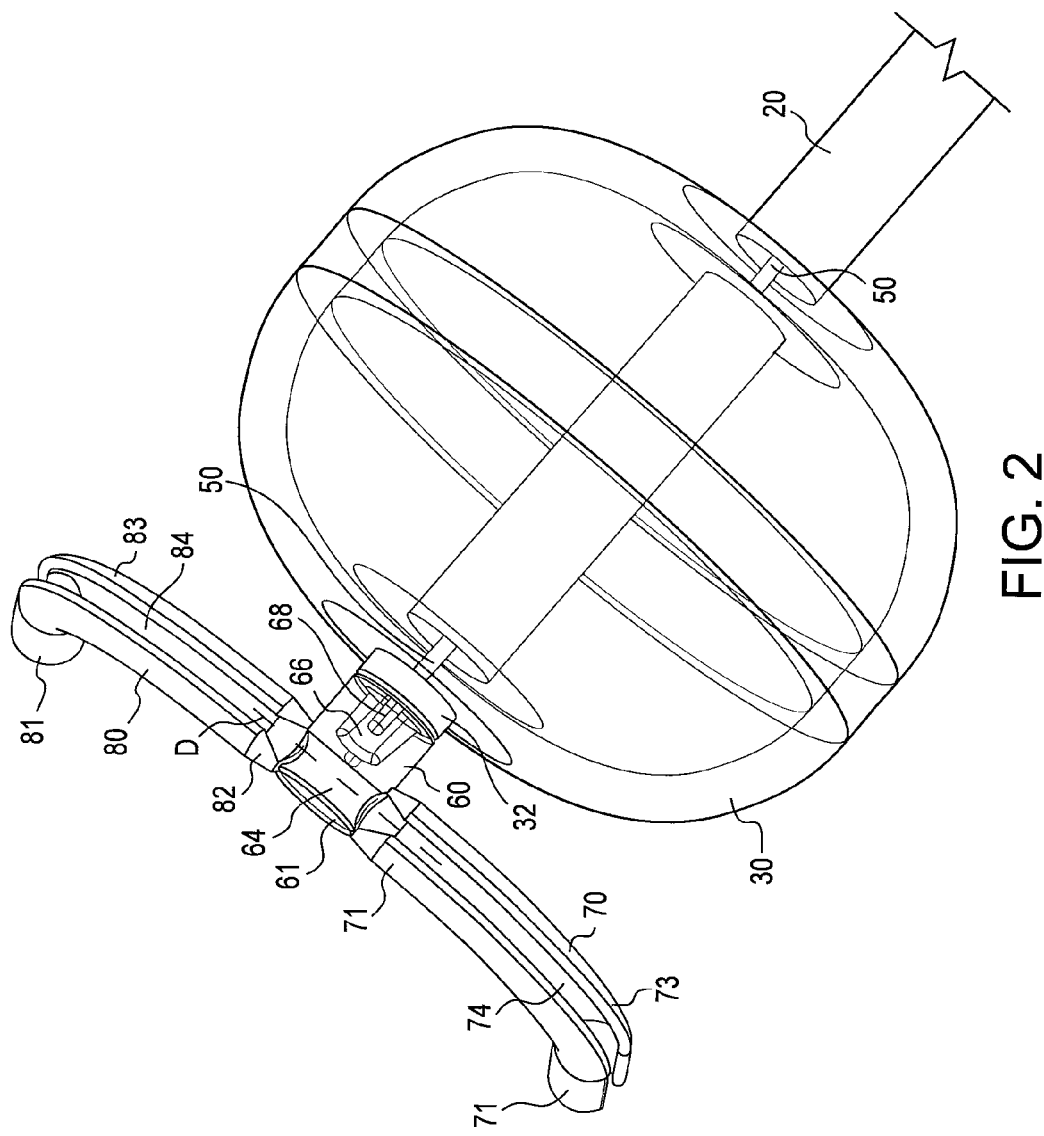
FIG. 2 is another prospective view of the cervical cerclage assistance device of FIG. 1.
Figure 3:
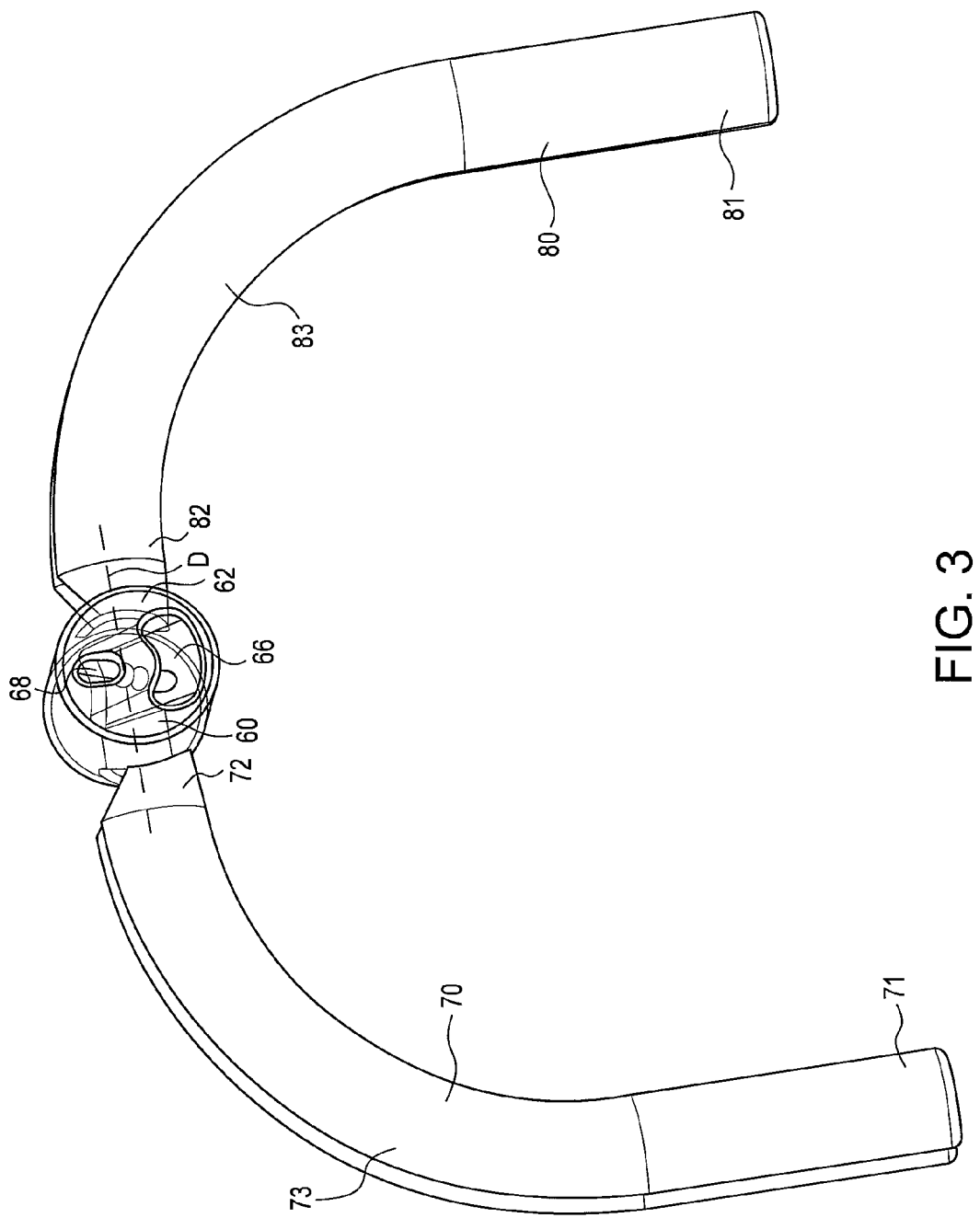
FIG. 3 is a perspective view of the barrier structure and first and second arms of the device of FIG. 1.
Figure 4:
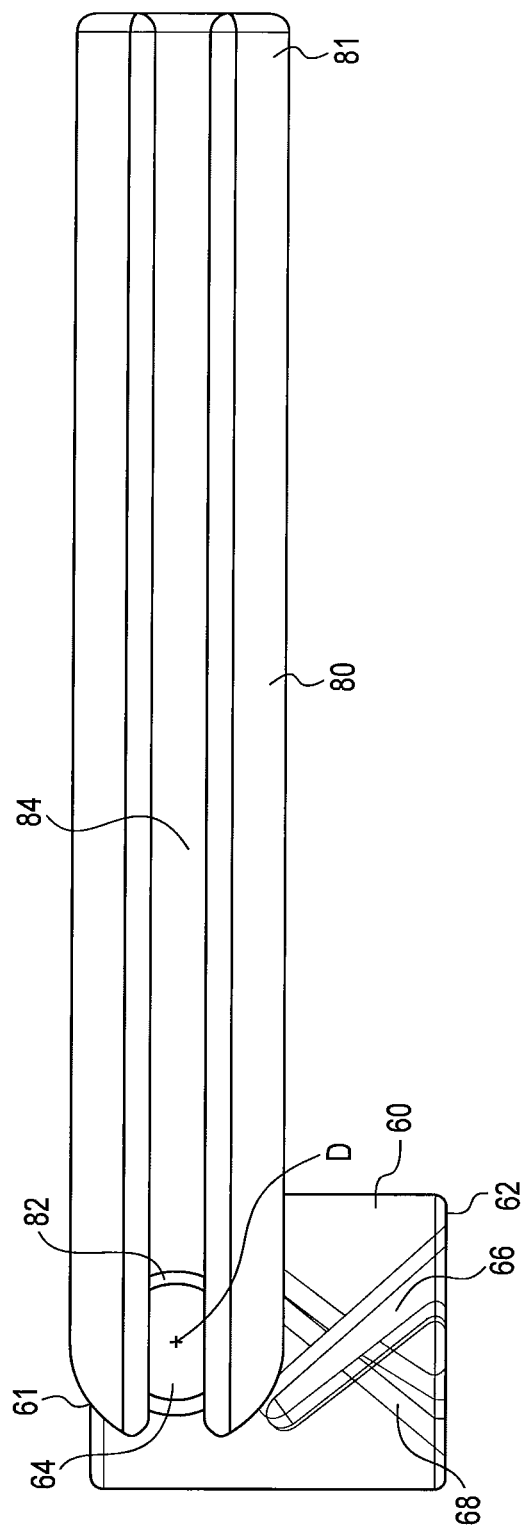
FIG. 4 is a side view of the second arm and barrier structure of the device of FIG. 1, showing the first and second blind holes of the barrier structure.
Figure 5:
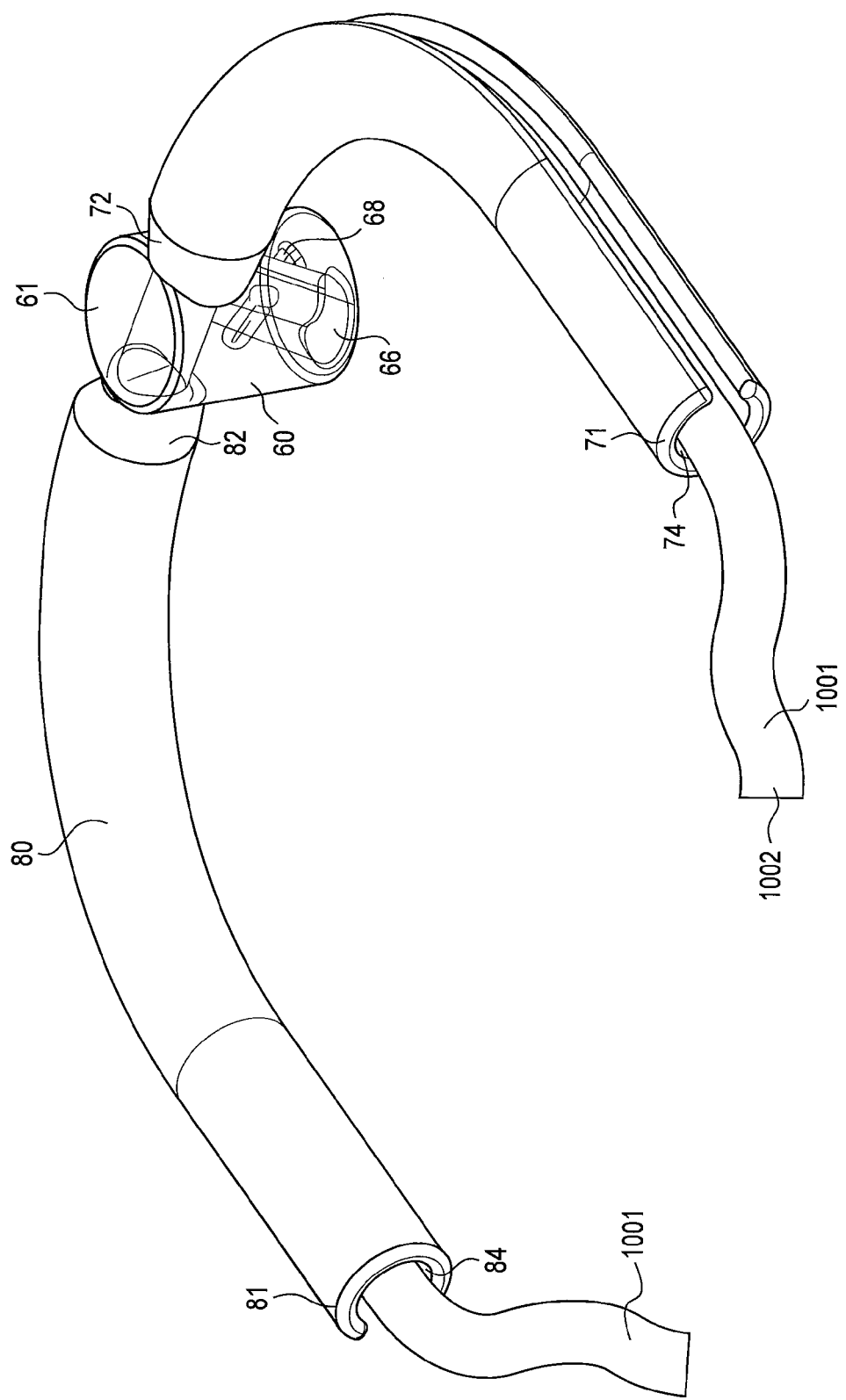
FIG. 5 is another perspective view of the barrier structure and first and second arms of the device of FIG. 1, showing an elongate tape threaded through the first and second arms and a through hole in the barrier structure.

As best shown in FIGS. 1-5, the barrier structure 60 may support one or more arms 70, 80 that extend therefrom and are sized and oriented to surround a portion of a patient's cervical tissue to assist with temporarily compressing the cervical tissue to allow the physician to easily and conveniently perform a cervical cerclage procedure. The arms 70, 80 are disposed such that their respective first ends 72, 82 (the ends that contact or are connected to the outer surface of the barrier structure 60) are each aligned with a through hole 64 disposed through the barrier structure 60, as best shown in by the common axis D. As best shown in FIGS. 2, 4, and 6, the through hole 64 is disposed substantially perpendicular to the longitudinal axis 60a of the barrier structure 60. In some embodiments, the through hole 64 may be generally parallel with a plane through one or both of the first and second holes 66, 68, while in other embodiments, best shown in FIG. 6, the through hole 64 is generally perpendicular to a plane through one or both of the first and second holes 66, 68. In still other embodiments, the through hole 64 may be disposed at an oblique angle with respect to a plane through one or both of the first and second holes 66, 68.

One or both of the first and second arms 70, 80 may be constructed with an central arcuate portion 73, 83, and may additionally be constructed with relatively straight portions at one or both of the first (inner) ends 72, 82 and the second (outer) ends 71, 81. Generally, the arms 70, 80 are constructed with a shape and size such that the arms are adapted to wrap around a significant portion of a female patient's (either human or mammal) cervical tissue when the device 10 is positioned such that the barrier structure 60 is disposed within or abutting the posterior formix 1104 of the patient's cervix (shown in FIG. 8). In some embodiments, the first and second arms 70, 80 are constructed to wrap around a significant portion of a patient's cervical tissue when the balloon 30 is inflated, which compresses the cervical tissue together due to the size of the inflated balloon, within the limited space available within the patient's vagina 1106.

Each of the first and second arms 70, 80 may have a substantially constant cross-section along their length, with some embodiments formed with a cross-section like a "C" along all or a portion of the length of the respective arm. In these embodiments, the first and second arms 70, 80 each include an internal volume 74, 84, which is configured to receive and allow a flexible member, such as a tape or mersilene band 1001 (shown schematically in FIG. 5), to be threaded therethrough. In some embodiments (best understood with reference to FIG. 5), the first and second arms 70, 80 are constructed such that the opening into the internal volume 74, 84 along the length of the arm is positioned such that the opening points generally away from the patient's cervical tissue 1102 (FIG. 8) when deployed within the patient. This construction has been found to be beneficial because it allows the tape 1001, discussed in detail below, to be partially removed from the arms 70, 80 when the arms 70, 80 engage the cervical tissue, to assist with tying or otherwise fixing the ends 1002 of the tape 1001 together.

The internal volume 74, 84 of each arm is configured to be in registry with the through hole 64 of the barrier structure 60, such that the tape 1001 may be threaded through the through hole 64 as well as the internal volume 74, 84 of each of the first and second arms 70, 80, and be staged for being positioned and temporarily secured around the patient's cervical tissue when the barrier structure is disposed at the proximal formix of the patient's cervix in preparation for the cervical cerclage procedure. In some embodiments, one or both of the first ends 71, 81 of the first and second arms 70, 80 are disposed coaxially with the through hole 64, as shown with axis D (FIG. 3). The tape 1001 may include a needle on one or both ends 1002 for engaging the opposite end 1002 of the tape 1001 for quickly fixing the tape 1001 around the cervix while applying compressing to the cervical tissue. In other embodiments, the ends of the tape 1001 may be tied together or otherwise fixed together to maintain the cervical tissue in compression.

In some embodiments, the barrier structure 60 may be formed without the first and second arms 70, 80, but otherwise is constructed like the barrier structure 60 discussed elsewhere herein. Specifically, the through hole 64 is configured to receive the tape 1001 therethrough, which is disposed in position to be wrapped around a patient's cervical tissue when the barrier structure 60 is disposed at the posterior formix 1104 of the patient's cervix, and the proper placement of the cervix to receive the tape 1001 may be provided when the balloon 30 is inflated. In embodiments without first and second arms 70, 80, the tape 1001 is pulled around the cervical tissue using a forceps or other appropriate devices to temporarily close the cervix in preparation for the cervical cerclage procedure.

Figure 8:
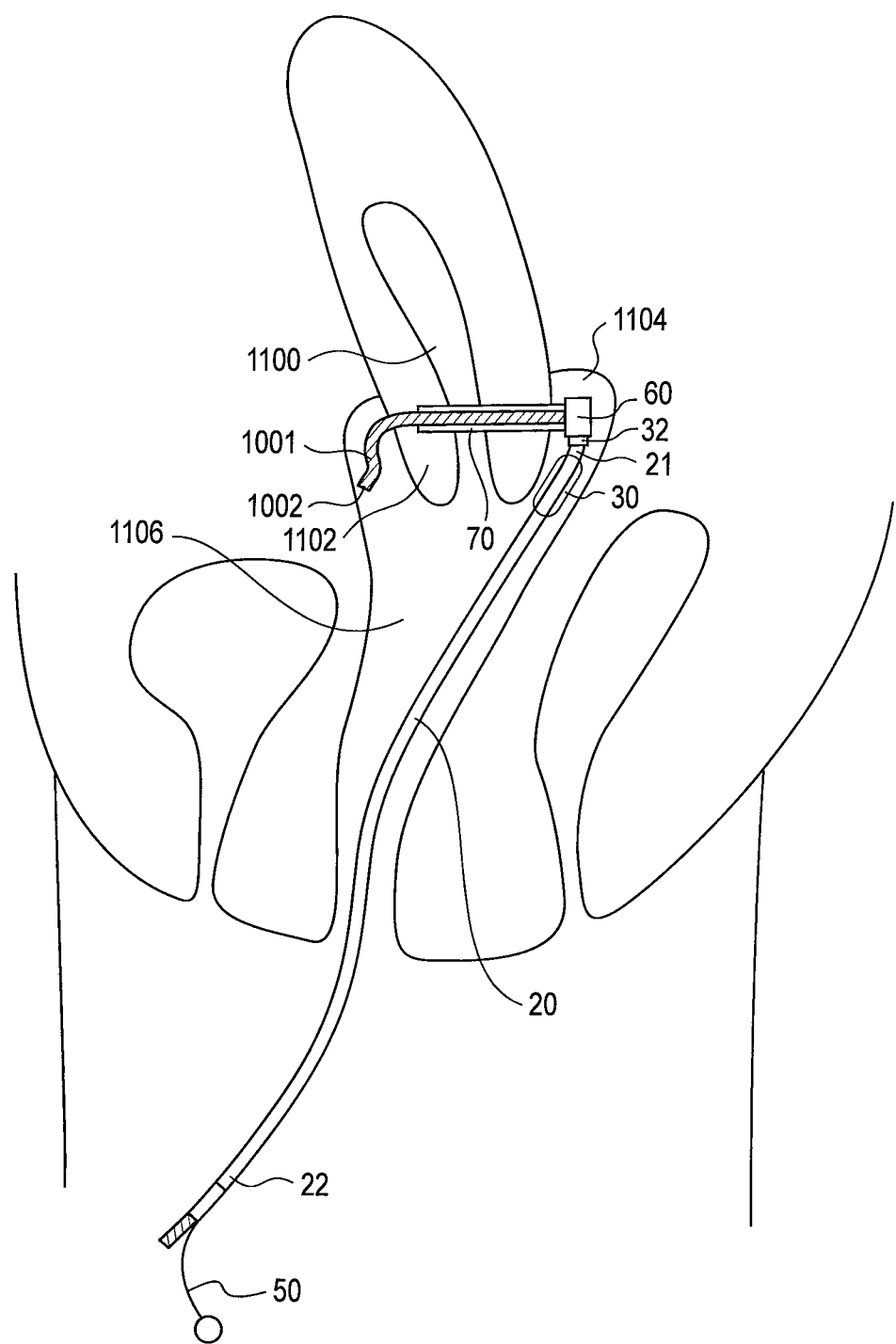
FIG. 8 is a side schematic view of a patient's vagina, cervix, and uterus, showing the device of FIG. 1 positioned therein in preparation for a cervical cerclage procedure.
Figure 9:
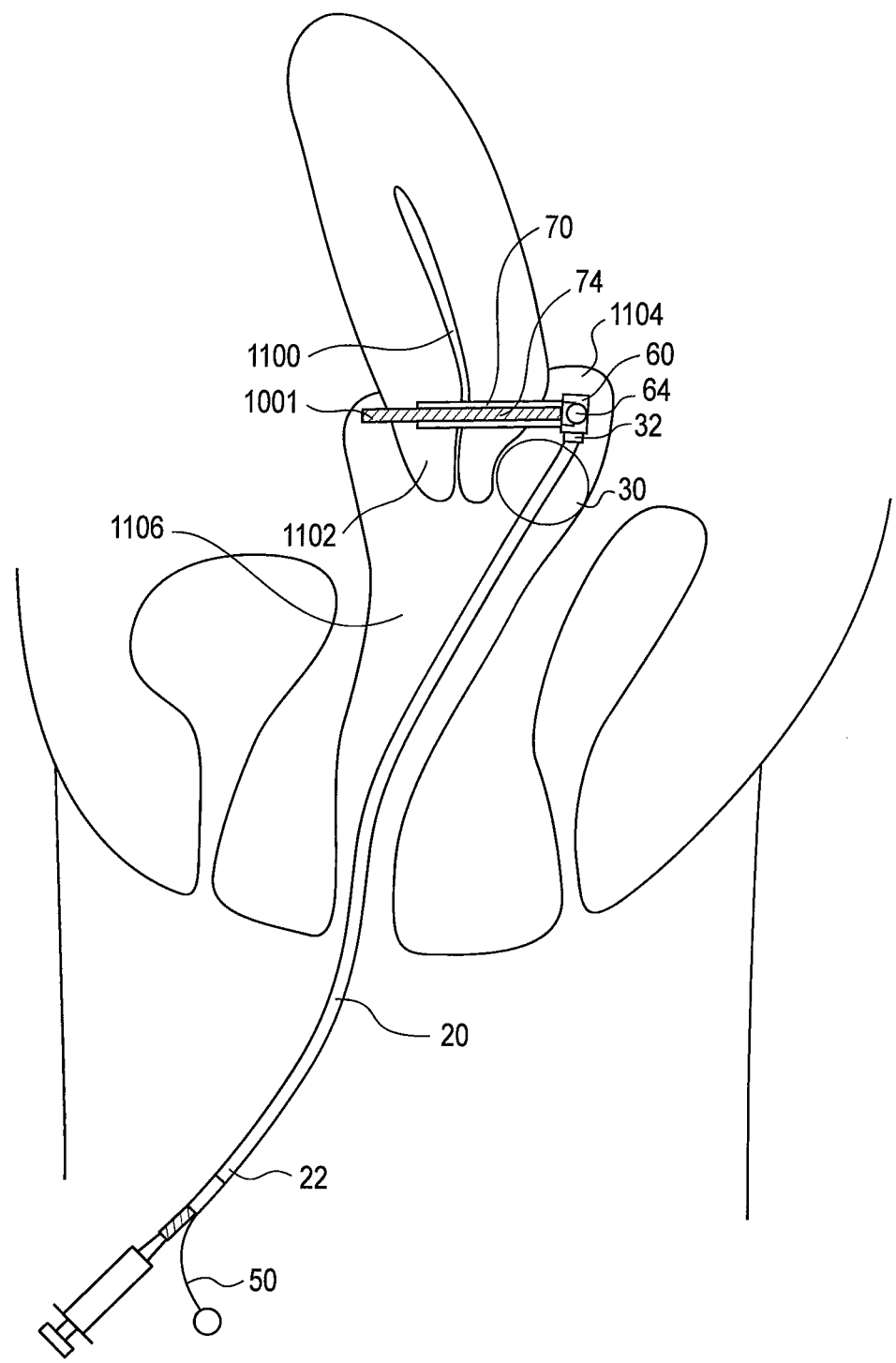
FIG. 9 is the view of FIG. 8 with the balloon expanded and the tape fixed to the cervical tissue.
Figure 10:
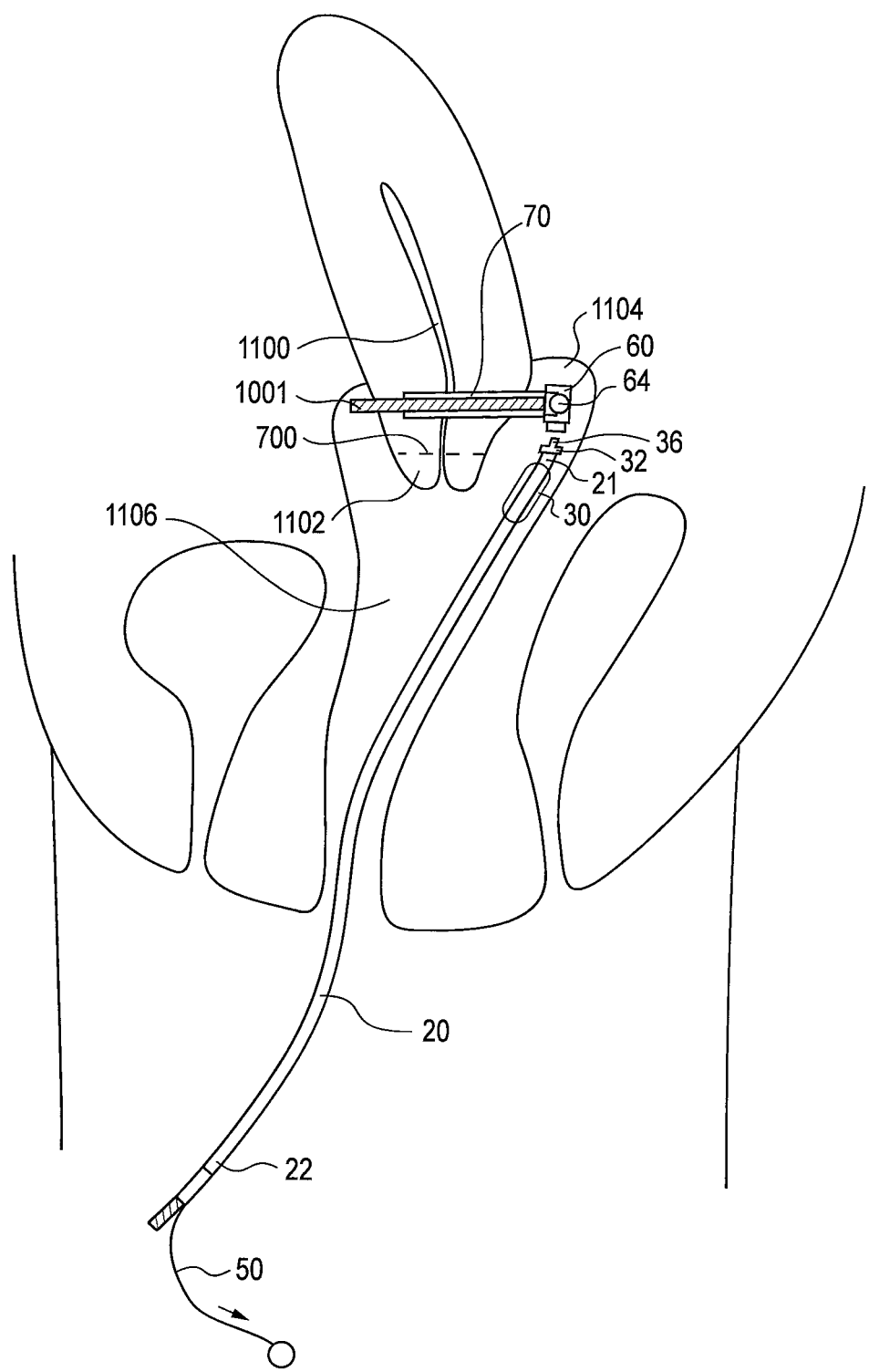
FIG. 10 is the view of FIG. 8 with the cervical cerclage stitching completed and the catheter released from the barrier structure.

Turning now to FIGS. 8-10, the device 10 is shown deployed within a patient's vagina 1106 with the barrier structure 60 proximate or within the posterior formix 1104 of a patient's cervix 1102. In FIG. 8, the barrier structure 60 is properly positioned, and the first arm 70 is around the patient's cervix 1102, and the second arm 80 (not visible with the view of FIG. 8) is wrapped around the opposite side of the patient's cervix 1102. As shown in FIG. 9, the balloon 30 may be inflated which compresses the cervical tissue 1102 together to prevent any communication from the vagina 1106 to the uterus 1100. As also shown in FIG. 9, the ends 1002 of the tape 1001 have been fixed together (shown schematically with a knot, but in some embodiments, a needle on one end of the tape 1001 may interact with the opposite end of the tape 1001 to fix the tape around the cervix 1102). The engagement of the tape 1001 (normally in tension) maintains the uterus 1100 closed due to the compression of the cervical tissue 1102, and after the tape 1001 is fixed around the cervix 1102, the balloon 30 may be deflated.

FIG. 10 depicts the catheter 20 disengaged from the barrier structure 60, which is fixed in position at the posterior formix 1104 due to the engagement of the tape 1001 around the cervical tissue 1102, and the threading of the tape 1001 through the through hole 64. As discussed above, the barrier structure 60 may be disengaged from the catheter 20 by pulling with the wire guide 50 proximally, as shown schematically by arrow W, at the proximal end portion 22 of the catheter 20. As best understood with reference to FIG. 6, as the wire guide 50 is pulled proximally, the distal tip 51 of the wire guide 50 slides though the second hole 68 in the barrier structure 60 and out of the first aperture 37 of the tip 36. After the wire guide 50 is pulled proximally, the catheter 20 is additionally pulled proximally (in the same direction as arrow W in FIG. 10) to withdraw the tip 36 from the first hole 66 of the barrier structure 60, and when the tip 36 is fully withdrawn from the first hole 66, the catheter 20 may be removed from the patient.

FIG. 10 further schematically depicts the cervical cerclage stitch upon the patient's tissue at 700. As discussed above, the cervical cerclage stitch may be the McDonald stitch, the Shirdokar stitch, or other types of stitch patterns known in the art. Upon completion of the desired (clinically) cervical cerclage procedure, the physician may cut or otherwise remove the tape 1001 from around the cervix, and withdraw the barrier structure 60, tape 1001, and first and second arms 70, 80 from the patient using a forceps or other tool.

Figure 11:
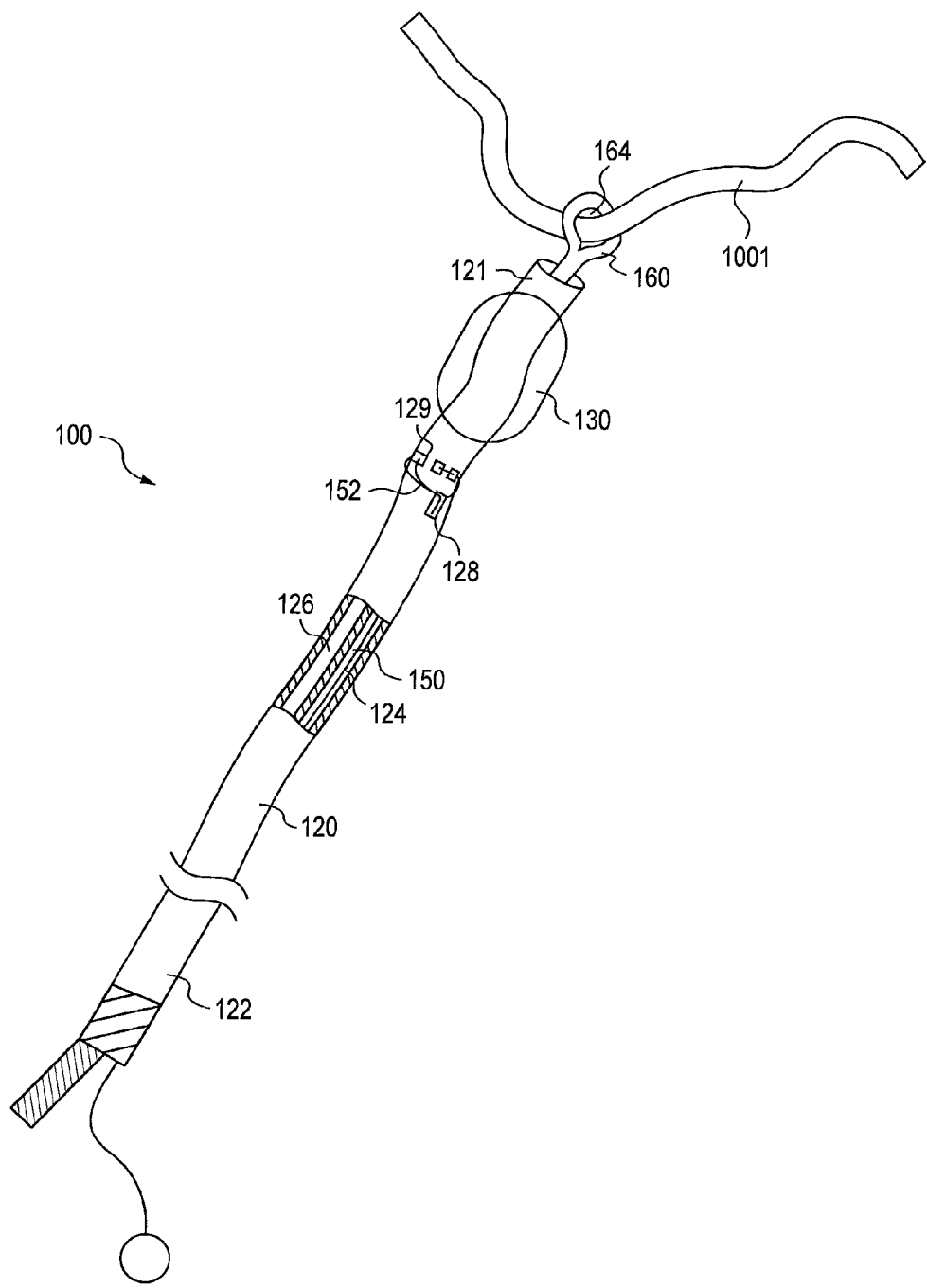
FIG. 11 is a perspective view of another embodiment of a cervical cerclage assistance device.
Figure 12:
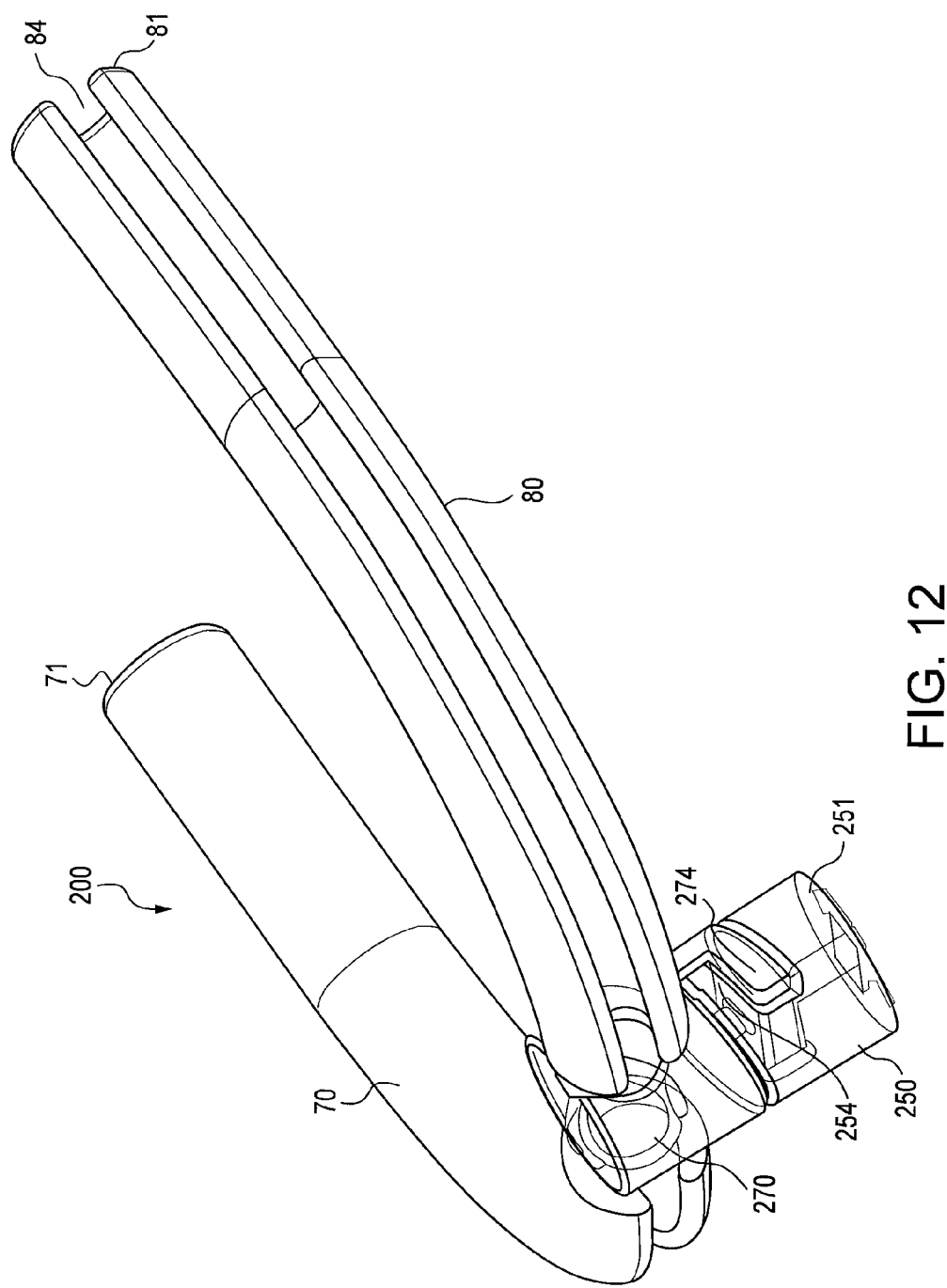
FIG. 12 is a perspective view of another embodiment of a cervical cerclage assistance device.

Turning now to FIG. 11, an alternate device 100 is provided. The device 100 includes an elongate catheter 120 that extends between a distal end portion 121 and a proximal end portion 122. The catheter 120 includes balloon 130, similar to balloon 30 discussed above, that may be inflated or deflated by injecting fluid therein through a balloon lumen 124 from a syringe or other fluid source through a luer lock or similar structure at the proximal end portion 122 of the catheter 120.

The end surface of the distal end portion 121 may receive another style barrier structure, such as an eyelet 160 or other similar structure with an aperture 164 therein, which allows a tape 1001 to be threaded therethrough, for engaging a patient's cervical tissue 1102 when the eyelet 160 is disposed at the proximal formix 1104 of the cervix 1102. In some embodiments, the eyelet 160 may additionally support one or more arms that are aligned with the aperture 164 of the eyelet 160, with the arms being constructed similarly to the two or more arms 70, 80 for engaging the cervical tissue when the eyelet 160 is properly positioned and the balloon 130 is inflated, as discussed above.

The catheter 120 may further include a second lumen 126 extending from the proximal end portion 122 of the catheter toward the distal end portion 121 of the catheter. The catheter 120 may further include a weakened region 129 upon the distal end portion 121 and distally of the balloon 130. The weakened region 129 may be formed from a portion of the catheter that has a thinner wall around the circumference thereof, may include a plurality of cuts along the circumference of the catheter 120 (either through the entire thickness of the material, or through only a portion of the thickness of the material), or in other known ways to form a circumference of the catheter 120 that is configured to easily break from the remainder of the catheter 120.

The second lumen 126 may communicate through the wall of the catheter 120 through one or more holes 128 formed either in the weakened region 129 or just proximal of the weakened region 129. In some embodiments, the one or more holes 128 may define at least a portion of the weakened region 129, while in other embodiments, the one or more holes 128 may be disposed proximally of the weakened region 129. The second lumen 126 may receive a wire guide 150 (such as a 0.032 inch wire guide) threaded therethrough, which extends therethrough from the proximal end portion 122 of the catheter and out the one or more holes 128. In other embodiments, the wire guide 150 may be other types of strong but thin wires, such as a piano wire or the like to allow the wire guide 150 to cut through the material forming the catheter 120 at the weakened region 129, as discussed below.

The wire guide 150 may form a loop 152 that is configured to interact with the weakened region 129, and configured to break the weakened region 129 when the wire guide 150 is pulled proximally at the proximal end portion 122 of the catheter 120. In some embodiments, the wire guide 150 may be woven through the plurality of holes defining the weakened region to form the loop 152, while in other embodiments, the loop 152 of the wire guide 150 may otherwise interact with the weakened region 129 to cut the material forming the catheter 120 at the weakened region 129 when the wire guide 150 is pulled. As understood with reference to the remainder of this specification, the device 100 is initially positioned with the eyelet 160 disposed proximate to or contacting the posterior formix 1104 of the patient's cervix, and the tape 1001 extending through the eyelet 160 (and arms, when provided) is wrapped around and tied (or otherwise fixed) around the cervix, while the cervical tissue is urged into positioned by the inflation of the balloon 130. Once the tape 1001 is fixed around the cervix, the wire guide 150 is pulled proximally, causing the wire guide 150 to cut through the weakened region 129, thus allowing the catheter 120 to be removed from the patient's vagina, with the tape 1001 remaining engaged with the cervix (and the eyelet 160 and remainder of the distal end portion 121 remaining within the patient. The physician next performs the cervical cerclage procedure and then cuts the tape 1001 and removes the tape 1001 and eyelet 160 from the patient.

Figure 13:
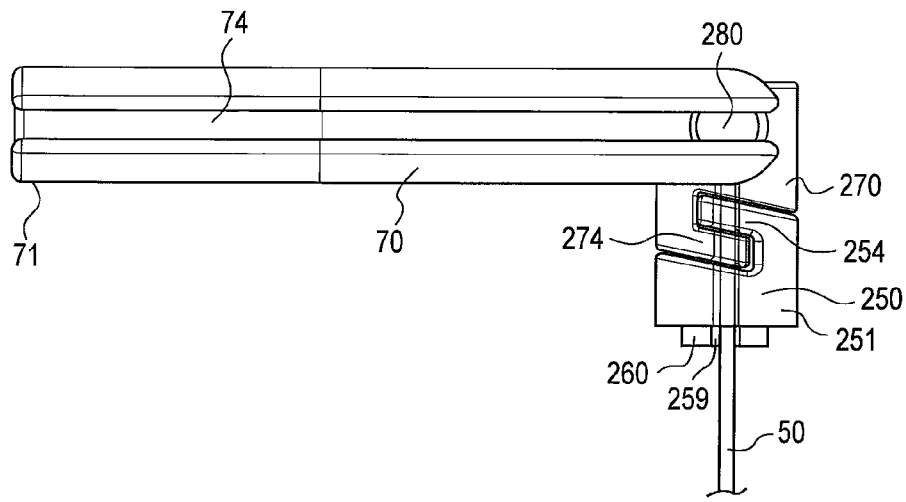
FIG. 13 is a side view of the device of FIG. 12, showing the barrier structure and hub maintained connected with a wire.
Figure 14:
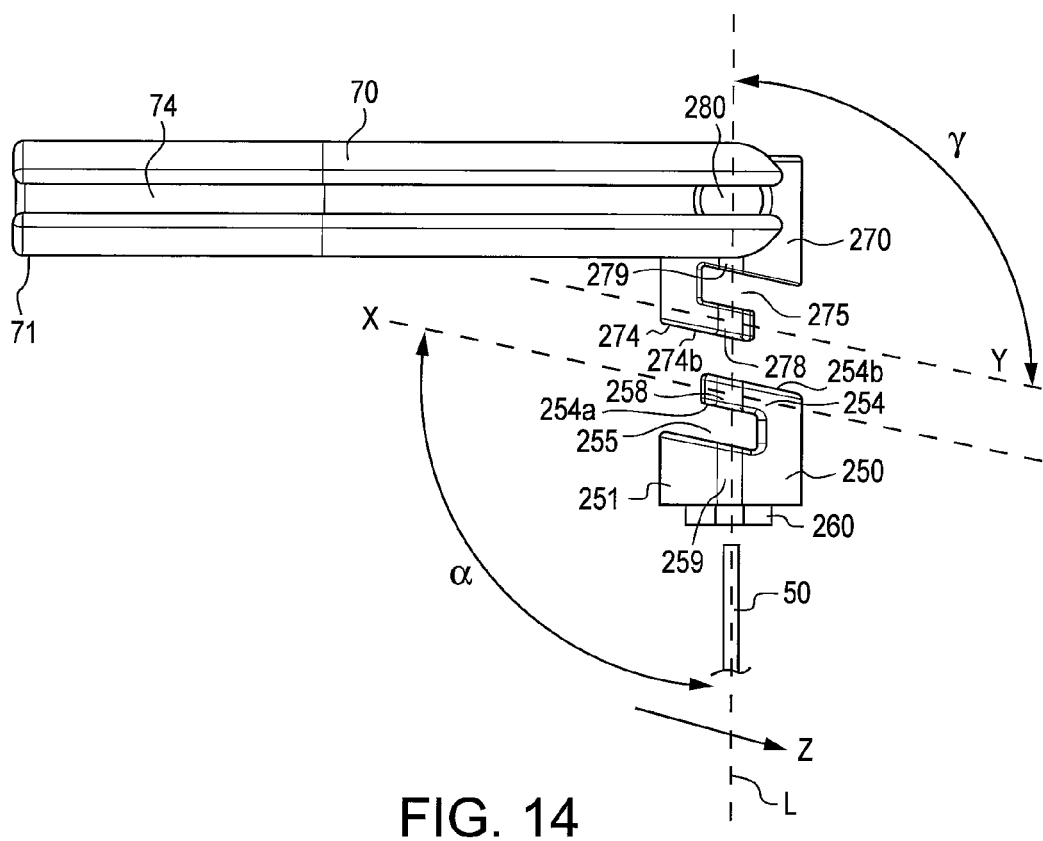
FIG. 14 is the view of FIG. 13 with the barrier structure disconnected from the hub with the wire removed.
Figure 15:
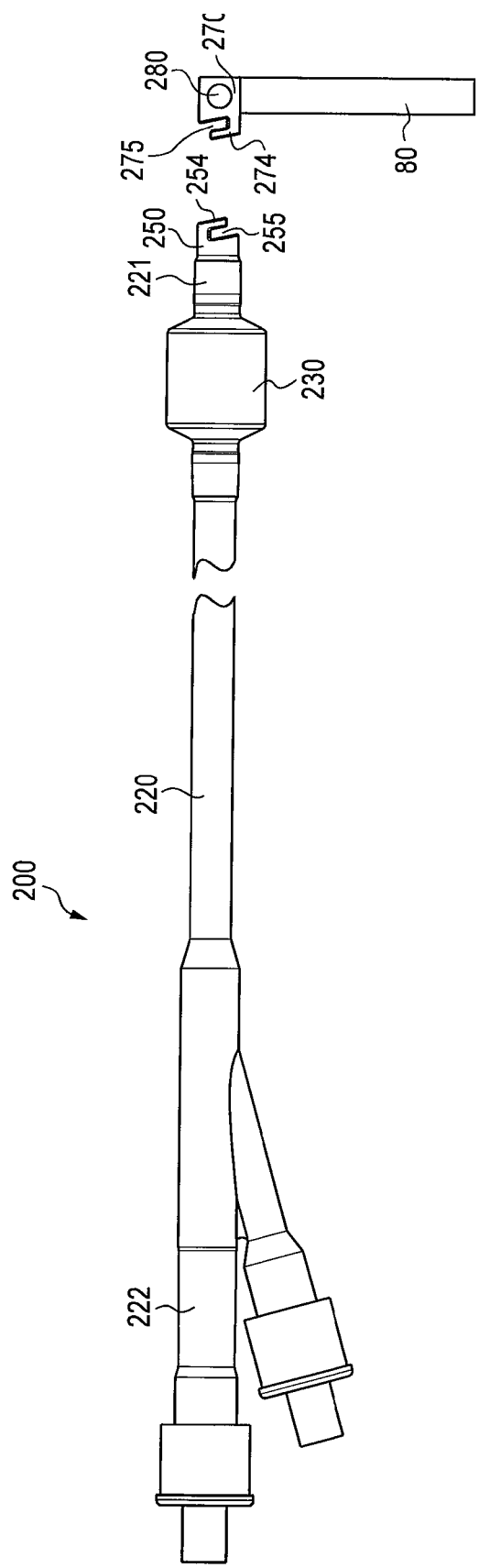
FIG. 15 is a side view of a catheter supporting the device of FIG. 12, with the barrier structure disconnected from the hub.
Figure 17:
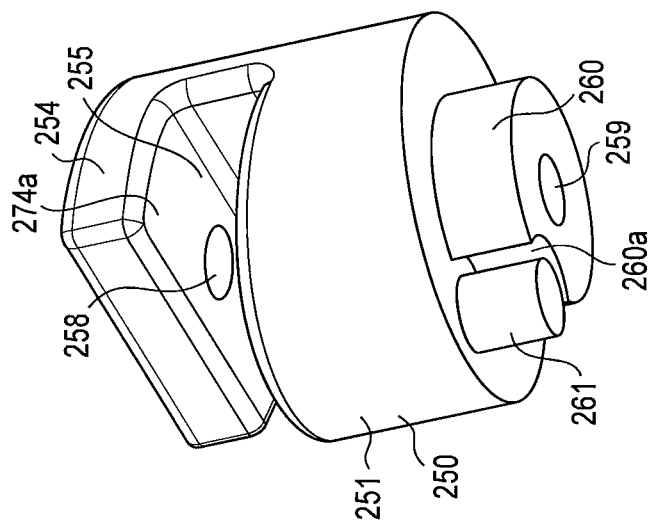
FIG. 17 is a perspective view of the hub of the device of FIG. 12.
Figure 16:
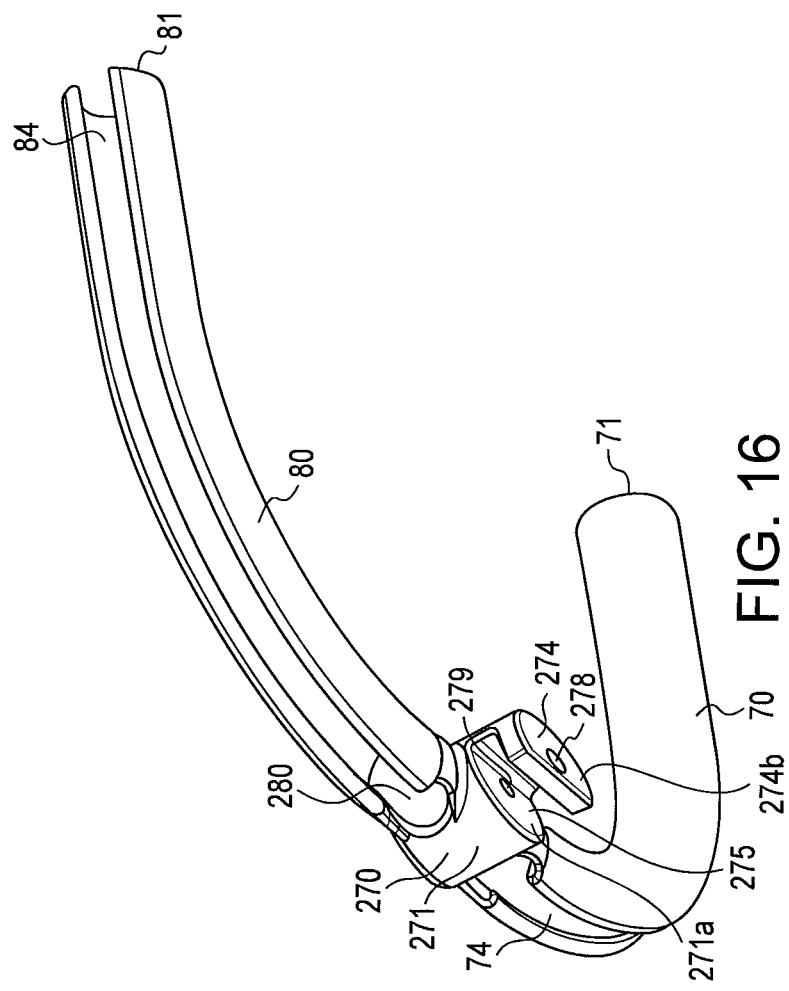
FIG. 16 is a perspective view of the barrier structure of the device of FIG. 12.

Turning now to FIGS. 12-17, another device 200 configured to a cervical cerclage procedure is provided. The device 200 includes an elongate catheter 220 that extends between a distal end portion 221 and a proximal end portion 222 (FIG. 15). The catheter 220 includes a balloon 230, similar to the balloon 30 discussed above, that may be inflated or deflated by injecting fluid therein through a lumen (not shown) from a syringe or other fluid source, as mated by a luer lock or similar structure disposed upon the proximal end portion 222 of the catheter 220.

The distal end portion 221 of the catheter may receive a hub 250 mounted thereto at the distal end face of the catheter. In some embodiments, the hub 250 may include a projection 260 that nests within a similar hole or void in the catheter 220, with the two components being fixed together with adhesive, with a press-fit or with other attachment methods. The projection 260 may be of a non-circular cross-section (such as with a bite or recess 260a) to provide for a single possible alignment between the hub 250 and the catheter 220. In some embodiments, the hub 250 may further include a plug 261, which may cap the balloon inflation lumen, as well as provide additional alignment structure between the hub 250 and the catheter 220.

The catheter 220 may include at least two lumens that extend from a proximal end portion 222 and in parallel through the length of the catheter 220 and to the distal end portion. A first lumen is configured to provide fluid communication between a luer lock adaptor and a balloon 230, which is disposed upon the distal end portion 221. The balloon 230 is configured to be inflated and deflated based upon the injection of fluid, such as water or saline into the balloon through the luer lock. The balloon 230 and the first lumen is similar to the balloon 30 and first lumen 26 discussed above. The catheter 220 may include a second lumen along its length between the proximal end distal end portions 222, 221, which allows a wire guide 50 or similar elongate, thin, flexible member therethrough. The second lumen of the catheter 220 is similar to the second lumen 24 discussed above. The second lumen is disposed coaxially and in communication with an aperture 259 through the hub 250, which is mounted to the distal end portion 221 of the catheter 220.

The hub 250 is fixed to the end face of the distal end portion 221 of the catheter 220. The hub 250 includes an extension 254 that extends from a body 251 of the hub 250. In some embodiments, the extension 254 extends in a direction away from the catheter 220, and defines a void 255 between the body 251 of the hub 250 and the inner surface of the extension 254. In some embodiments as shown on FIG. 14, the extension 254 may extend from the body 251 of the hub 250 along an axis X that extends in an obtuse angle α to the longitudinal axis L of the hub 250 (or the axis of the aperture 259). In some embodiments, the angle α may be between about 100 and about 135 degrees (inclusive of all angles within this range), while in other embodiments, the angle α may be about 100 to about 120 degrees (inclusive of all angles within this range). The inner surface 254a of the extension 254 (i.e. the surface facing the body 251 of the hub 250 may be parallel to an axis through the hub 250.

In some embodiments, the upper surface of the body 251 of the hub 250 may be parallel with the extension 254, such that the void 255 (and both the surfaces of the body 251 and the extension 254 that define the void 255) of the hub 250 extends in the same angle α as the extension 254 with respect to the longitudinal axis L of the hub 250. In some embodiments, the upper surface 254b of the extension 254 is also parallel with the extension 254 (and in some embodiments the lower surface 254a). The extension 254 additionally includes a hole 258 that is coaxial with the aperture 259 in the body 251 of the hub 250. The hole 258 is configured such that a wire guide 50 that extends through the catheter 220 and the aperture 259 of the hub 250 additionally extends through the hole 258 in the extension 254.

The barrier structure 270 is additionally provided and is removably attached to the hub 250. The barrier structure 270 may retain one or more arms 70, 80 thereon, which may be the same (in operation and/or structure) as the arms 70, 80 discussed above and are configured to support a tape or band 1001 for use in conjunction with a cervical cerclage procedure as discussed above. The barrier structure 270 includes a base 271 that defines a hole 280 that is aligned with the first and second arms 70, 80 (or one of the first or second arms 70, 80 in embodiments where only one arm 70 80 is provided) such that a tape or band 1001 that is threaded through the hole 280 additionally is threaded through the first and/or second arms 70, 80.

The barrier structure 270 additionally includes a finger 274 that extends from the base 271 of the barrier structure 270. The finger 274 may extend from the base 271 such that an axis Y through the finger 274 extends at the angle γ to the longitudinal axis L through a first hole 278 through the finger 274 and a coaxial hole 279 that extends blindly into the base 271 of the barrier structure 270. In some embodiments the angle γ may be the same or similar to the angle α, while in other embodiments it may be different. In embodiments where the angles γ and α are different, the finger 274 and the extension 254 fit together (discussed in more detail below) with the various sizes and shapes of the finger 274 and extension 254 (as well as the two voids 275, 255, to allow engagement between the barrier structure 270 and the hub 250.

The finger 274 defines a second void 275 between an inner surface 274a of the finger 274 and a bottom surface 271a of the base. The second void 275 is sized to receive the extension 254 therein and the first void 255 is sized to receive the finger 274 therein, such that the barrier structure 270 and the hub 250 are removably connected together. When the barrier structure 270 and the hub 250 are connected together, a wire guide 50 may extend through the lumen of the catheter 220, through the aperture 259 of the hub 250, through hole 278 in the finger 274, then through the hole 258 in the extension and finally within the blind hole 279 within the barrier structure 270. The extension of the wire guide 50 through the plurality of aligned holes when the barrier structure 270 is fixed to the hub 250 (and therefore the catheter 220) prevents disconnection because the wire guide 50 prevents the finger and extension 274, 254 from sliding out of the respective void 255, 275.

The barrier structure 270 can be decoupled or disconnected from the hub 250 when the wire guide 50 is withdrawn from the barrier structure 270 (including the finger 274 as well as the extension 254. The withdrawal of the wire guide 50 allows each of the finger 274 and extension 254 to be able to be slid out of the void (255, 275) on the opposite component, which decouples the barrier structure 270 from the catheter 220.

As discussed elsewhere herein, the device 200 is configured to assist with the performance of a cervical cerclage procedure, and the device 200 is used clinically in a similar manner to the device 10 discussed above. The steps discussed above and depicted in FIGS. 8-10 are equally applicable with the device 200 as with the device 10 (with the structural differences of the connection between the barrier structure 60 and the catheter 20 and the barrier structure 270 and the catheter 220 causing a difference in response when the wire guide 50 is pulled proximally with both embodiments, with these difference easily appreciated with a thorough review of the subject specification and figures).

As will be understood with reference to FIGS. 13 and 14, when the wire guide 50 is withdrawn from the barrier structure 270 and the extension 254 of the hub 250, the barrier structure 270 may be released from the hub 250 and the catheter 220. As can be understood, the two structures are released when the catheter 220 and hub 250 are moved sideways (i.e. in the direction Z of FIG. 14), which causes the extension 254 to slide out of the void 275 and causes the finger 274 to slide out the void 255. Upon removal of the hub 250 from the barrier structure 270, the catheter 220 is withdrawn from the patient, and the barrier structure can be removed from the patient after the cervical stitch(s) are completed and the tape or band 1001 is cut.

While the preferred embodiments of the disclosure have been described, it should be understood that the disclosure is not so limited and modifications may be made without departing from the disclosure. The scope of the invention is defined by the appended claims, and all devices that come within the meaning of the claims, either literally or by equivalence, are intended to be embraced therein.

The invention claimed is:

1. A medical device configured for assistance with the cervical cerclage procedure, comprising:
    a barrier structure includes a finger that extends from a base of the barrier structure to define a first void between the finger and the base, wherein a first hole extends through both the finger and blindly through a portion of the base;
    a hub fixed to a distal portion of an elongate catheter, the hub comprising an extension that extends from an end surface of the hub to define a second void between the end surface of the hub and the extension, wherein a lumen extends through the catheter and further communicates through a second hole through the hub and the extension;
    wherein the barrier structure and hub are configured to mate together such that the extension extends within the first void and the finger extends within the second void, and such that the lumen, the second hole, and the first hole are coaxially aligned,
    wherein the barrier structure supports first and second arms that each extend outwardly from a side surface of the barrier structure, wherein each of the first and second arms include an internal volume that extends along a length of each respective arm,
    further comprising a through hole in the barrier structure that is disposed substantially perpendicular to a longitudinal axis of the barrier structure, wherein the internal volume of each of the first and second arms is disposed in registry with the through hole.

2. The medical device of claim 1, wherein each of the lumen, the first hole, and the second hole are configured to receive a wire guide therethrough when the barrier structure and hub are mated together.

3. The medical device of claim 2, further comprising a wire guide withdrawably extending through the lumen, the first hole, and the second hole when the barrier structure and hub are mated together, wherein the finger is releasable from the second void to separate the hub and barrier structure when the wire guide is withdrawn from the first hole and the second hole.

4. The medical device of claim 1, wherein the catheter further comprises an inflatable balloon disposed upon a distal end portion of the catheter.

5. The medical device of claim 1, wherein the first and second arms are configured to substantially surround a patient's cervix when the barrier structure is disposed contacting or proximate to a posterior fornix of the patient's cervix.

6. The medical device of claim 5, further comprising a flexible band that extends through the internal volume of each of the first and second arms.

7. The medical device of claim 6, wherein the flexible band comprises opposite first and second ends that extend beyond distal ends of the respective first and second arms.

8. The medical device of claim 7, wherein the first and second ends of the flexible band are configured to be fixed together when the flexible band is disposed around the patient's cervix.

9. The medical device of claim 5, wherein the first and second arms are configured to continue to surround the patient's cervix when the barrier structure and the hub are disengaged from each other by withdrawing the extension from the first void and withdrawing the finger from the second void.

10. The medical device of claim 1, wherein the first and second arms extend from the barrier structure proximate to opposite ends of the through hole.

11. A medical device configured for assistance with the cervical cerclage procedure, comprising:
   a barrier structure includes a finger that extends from a base of the barrier structure to define a first void between the finger and the base, wherein a first hole extends through the finger and blindly through a portion of the base;
   a hub fixed to a distal portion of an elongate catheter, the hub comprising an extension that extends from an end surface of the hub to define a second void between the end surface of the hub and the extension, wherein a lumen extends through the catheter and further communicates through a second hole through the hub and the extension,
   the catheter further comprises an inflatable balloon disposed upon a distal end portion of the catheter;
   wherein the barrier structure and hub are configured to mate together such that the extension extends within the first void and the finger extends within the second void, and such that the lumen, the second hole, and the first hole are coaxially aligned,
   wherein the barrier structure further comprises a first aperture that is disposed therethrough, and a flexible band that is received through the first aperture, the flexible band being configured to surround a patient's cervix when the barrier structure is disposed in contact with or proximate to a posterior fornix of the patient's cervix.

12. The medical device of claim 11, wherein the balloon is inflatable while the barrier structure and hub are retained in a mated together configuration, and the barrier structure and the hub can be disengaged independently of the balloon.

13. The medical device of claim 11, wherein the first aperture is disposed substantially perpendicular to a longitudinal axis of the barrier structure.

14. The medical device of claim 11, wherein the flexible band includes opposite first and second ends that extend from opposite sides of the first aperture, the first and second ends being configured to be fixed together when the flexible band is disposed around the patient's cervix.

15. The medical device of claim 14, wherein the flexible band is configured to continue to be disposed around the patient's cervix when the barrier structure and the hub are disengaged from each other by withdrawing the extension from the first void and withdrawing the finger from the second void.

* * * * *